(12) United States Patent
Linnes et al.

(10) Patent No.: US 12,029,548 B2
(45) Date of Patent: Jul. 9, 2024

(54) DEVICE FOR SELECTIVE COLLECTION AND CONDENSATION OF EXHALED BREATH

(71) Applicant: Purdue Research Foundation, West Lafayette, IN (US)

(72) Inventors: Jacqueline C. Linnes, West Lafayette, IN (US); Divya Tankasala, West Lafayette, IN (US); Shubhankar S. Takle, West Lafayette, IN (US); Orlando S. Hoilett, West Lafayette, IN (US); Gabriel P. Ng, West Lafayette, IN (US); Michael S. Smith, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 735 days.

(21) Appl. No.: 17/251,254

(22) PCT Filed: Jun. 18, 2019

(86) PCT No.: PCT/US2019/037631
§ 371 (c)(1),
(2) Date: Dec. 11, 2020

(87) PCT Pub. No.: WO2020/009798
PCT Pub. Date: Jan. 9, 2020

(65) Prior Publication Data
US 2021/0251514 A1    Aug. 19, 2021

Related U.S. Application Data

(60) Provisional application No. 62/693,001, filed on Jul. 2, 2018.

(51) Int. Cl.
*A61B 5/097* (2006.01)
*A61B 5/08* (2006.01)
*A61B 5/145* (2006.01)

(52) U.S. Cl.
CPC .............. *A61B 5/097* (2013.01); *A61B 5/082* (2013.01); *A61B 5/14532* (2013.01)

(58) Field of Classification Search
CPC ...... A61B 5/097; A61B 5/082; A61B 5/14532
See application file for complete search history.

(56) References Cited

U.S. PATENT DOCUMENTS

| 2007/0173731 A1* | 7/2007 | Meka ................... G01N 33/497 |
| | | 600/543 |
| 2010/0241019 A1* | 9/2010 | Varga ..................... A61B 5/082 |
| | | 600/532 |

(Continued)

OTHER PUBLICATIONS

PCT/US2019/037631, the International Search Report and the Written Opinion of the International Searching Authority, Sep. 4, 2019.

*Primary Examiner* — Daniel L Cerioni
*Assistant Examiner* — Ari Singh Kane Padda
(74) *Attorney, Agent, or Firm* — Purdue Research Foundation

(57) ABSTRACT

The present disclosure relates to a novel device for selective collection and condensation of an exhaled breath, and the method of using the novel device. The novel device is portable and capable of collecting and condensing reproducible volumes of exhaled breath under about 10 minutes by using a unique temperature-based algorithm.

9 Claims, 5 Drawing Sheets

(56) References Cited

U.S. PATENT DOCUMENTS

2010/0292601 A1* 11/2010 Dompeling ............ A61B 5/411
                                                    600/543
2017/0119279 A1   5/2017 Ahmad et al.
2017/0119280 A1*  5/2017 Ahmad .................. A61B 5/097
2017/0196481 A1   7/2017 Rundell et al.
2018/0156775 A1*  6/2018 Chou ................... G01N 1/2813

* cited by examiner

DEVICE FOR SELECTIVE COLLECTION AND CONDENSATION OF EXHALED BREATH

CROSS REFERENCE

The present U.S. patent application is a national stage entry under 35 U.S.C. § 371(b) of International Application No. PCT/US19/37631, filed on Jun. 18, 2019, which is related to and claims the priority benefit of U.S. Provisional Application No. 62/693,001, filed Jul. 2, 2018, the content of which is hereby incorporated by reference in its entirety.

GOVERNMENT RIGHTS

This invention was made with government support under National Institutes of Health (NIH) Award No. 1R21EB024733 and P30DK097512 awarded by National Institutes of Health. The United States government has certain rights in the invention.

TECHNICAL FIELD

The present disclosure relates to novel device for selective collection and condensation of exhaled breath, and the method of using the device.

BACKGROUND

This section introduces aspects that may help facilitate a better understanding of the disclosure. Accordingly, these statements are to be read in this light and are not to be understood as admissions about what is or is not prior art.

Non-invasive methods for detection and monitoring of diseases are key in ensuring patient compliance and access. Small molecule analytes, such as glucose, provide valuable insight into patient health at the point-of-care. While self-monitoring of blood glucose is critical to properly controlling diabetes, 67% of patients fail to monitor their glucose levels due to the inconvenience of collecting finger-prick blood samples. Alternative samples including interstitial fluid, sweat, tears, aqueous humor, saliva, and exhaled breath condensate (EBC), also contain glucose, although at concentrations that are orders lower than that of blood.

EBC is a promising non-invasive sample for glucose monitoring purposes due to its highly controlled physiological regulation. The respiratory fluid present in the alveolar epithelial lining contains glucose concentrations that are 3-20 times lower than that of plasma glucose due to the rapid glucose exchange between lung fluid and blood. However, this concentration is further diluted by additional water vapor exhaled during respiration when collected as EBC. Anatomical dead space air is defined as the portion of air from the upper respiratory tract (e.g. mouth, nose, and trachea) that does not participate in gas exchange and thus does not contain analytes from alveolar epithelial lining from the respiratory fluid. The inclusion of dead space air in collected EBC samples and inconsistent collection methods have contributed to the wide range in experimental blood-to-breath glucose ratios, which range anywhere from 1000:1 to 50,000:1.

The most common collection procedure for EBC involves the rapid cooling of exhalate and the subsequent condensation of the water vapor phase that allows aerosol particles to adhere to cooled inert surfaces such as silicone or Teflon. Commercially-available collection systems such as the RTube and ECoScreen do not account for the separation of dead space air from deep lung air because most EBC analyses are focused on lung disease biomarkers not restricted to respiratory fluid. By selectively collecting only exhaled breath that has been exchanged with lung fluid, it is anticipated that a greater fraction of glucose can be collected in the condensate. Novel device and method for selective collection and condensation of exhaled breath for the detection of chemicals related to certain health conditions are therefore needed.

SUMMARY

The present disclosure relates to novel device for selective collection and condensation of exhaled breath, and the method of using the device.

In one embodiment, the present disclosure provides a device for selective collection of exhaled breath condensate for glucose detection, wherein the device comprises:
a) an input configured to receive an exhaled breath from a human subject, wherein said exhaled breath comprises a first portion that is not deep lung air, and a second portion that is deep lung air, wherein said deep lung air comprises at least one chemical to be detected;
b) a first output configured to release said first portion of said exhaled breath that is not deep lung air;
c) a second output configured to collect said second portion of said exhaled breath that is deep lung air, wherein said deep lung air comprises at least one chemical to be detected;
d) a sensor capable of detecting temperature;
e) a valve configured to be positioned between said input, said first output, and said second output, wherein said valve is actuated by a temperature-based algorithm to selectively release said first portion of said exhaled breath, and selectively collect said second portion of said exhaled breath; and
f) a collection unit configured to collect and condense said second portion of said exhaled breath.

DETAILED DESCRIPTION

Figure 1:
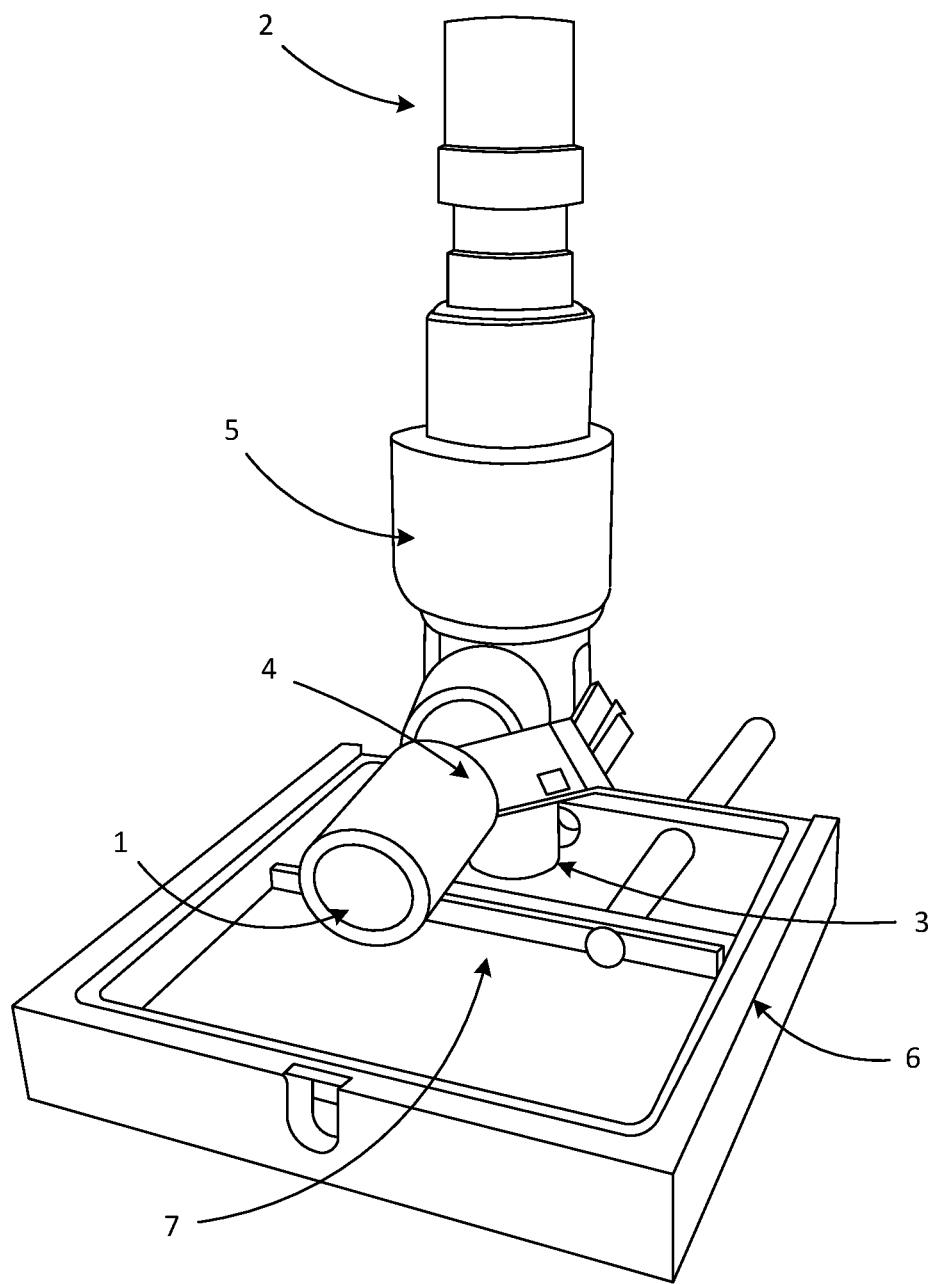
FIG. 1 is a selective EBC collection device pictured with T-Valve, embedded Rev. C Wind Sensor, condensation plate with collection frame, and built-in squeegee (1. Mouthpiece as an input; 2. Exhaust port as a first output; 3. Intake Port as a second output; 4. Sensor; 5. T-Valve; 6. Sample collection unit; 7. Squeegee).

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "chemical" and/or "analyte" may refer to any organic and/or inorganic material found in an exhaled breath condensate sample from a subject/person to be examined. The existence of such organic and/or inorganic material in the exhaled breath condensate may serve as a marker/biomarker for the identification of certain disease, symptoms, and/or drug uses of a subject/person that is examined. A "chemical" and/or "analyte" may be but is not limited to glucose, nucleic acid, protein, peptide, lipid, inositol, cytokine, acid, amylase, lipoarabinomannan, interferon gamma, nitrite, pathogen, hydrogen peroxide, opioid, nicotine salt, lactate, or any combination thereof.

The present disclosure provides novel, low-cost, selective condenser device for collecting and condensing defined volumes of exhaled breath derived from deep lung air. The device uses a unique temperature-based algorithm to actuate a selective valve opening; bypassing the need for expensive end-tidal $CO_2$ sensors. The condensate collected from this device provides a robust sample for evaluating glucose concentrations as well as other analytes of interest such as inositols, inflammatory markers, and peptide biomarkers collected in the condensate.

In one embodiment, the present disclosure provides a device for selective collection of exhaled breath condensate for glucose detection, wherein the device comprises:
  a) an input configured to receive an exhaled breath from a human subject, wherein said exhaled breath comprises a first portion that is not deep lung air, and a second portion that is deep lung air, wherein said deep lung air comprises at least one chemical to be detected;
  b) a first output configured to release said first portion of said exhaled breath that is not deep lung air;
  c) a second output configured to collect said second portion of said exhaled breath that is deep lung air, wherein said deep lung air comprises at least one chemical to be detected;
  d) a sensor capable of detecting temperature;
  e) a valve configured to be positioned between said input, said first output, and said second output, wherein said valve is actuated by a temperature-based algorithm to selectively release said first portion of said exhaled breath, and selectively collect said second portion of said exhaled breath; and
  f) a collection unit configured to collect and condense said second portion of said exhaled breath In one embodiment, said temperature-based algorithm is used to control collection of said second portion of said exhaled breath when two successive decreases in temperature are recorded.

In one embodiment, said temperature-based algorithm is used to control open and close of said valve, wherein said valve opens when the difference between current temperature and temperature at the start of the exhalation period exceeds the calculated threshold and closes after two successive temperature decreases.

In one embodiment, the chemical to be collected and tested comprises glucose, nucleic acid, protein, peptide, lipid, inositol, cytokine, lipoarabinomannan, interferon gamma, nitrite, pathogen, hydrogen peroxide, or any combination thereof. In one aspect, the chemical is glucose.

In one embodiment, the condensation unit of the device has a temperature range of −20° C. to 15° C. In one aspect, the temperature range is 5° C. to 15° C.

In one embodiment, the valve used in the device may be but is not limited to pneumatic valve, solenoid valve, or any valve that can be controlled to open and close to selectively control collection of a passing flow.

In one embodiment, the present disclosure provides a method of collecting at least one chemical to be detected, wherein the method comprises the use of the device of the present disclosure. In one aspect, the method comprises providing a device of the present disclosure to a human subject, collecting an exhaled breath from the human subject through an input; releasing an first portion of said exhaled breath that is not deep lung air to a first output of the device; collecting a second portion of said exhaled breath that is deep lung air, wherein said deep lung air comprises at least one chemical to be detected, wherein the second portion of said exhaled breath is collected with a second output of the device, wherein a valve is configured to be positioned between said input, said first output, and said second output, wherein said valve is actuated by a temperature-based algorithm to selectively release said first portion of said exhaled breath, and selectively collect said second portion of said exhaled breath.

I. Device Design

The goal of the present disclosure was to create a device that can efficiently collect and cool condensate from within the deep lung respiratory circuit while being portable and easy to use for both the assisting nurse and the patient. Apart from being able to selectively collect exhaled breath participating in alveolar fluid exchange, other design parameters of the device included a robust valve with limited airflow resistance for ease of breathing, a large surface area for condensate formation, the ability to collect and quantify the total volume of air exhaled, and a low profile for portability and ease-of-use.

I.A. Valve Design for Selective Collection of Exhaled Breath

The selective EBC collection valve within this device is an electrically actuated pneumatic T-Valve (Hans-Rudolph, Kansas, USA). The valve has one input to receive breath and two outputs: one for intake to the collection chamber when the user's breath is composed of deep lung air, and one for exhaust of the first portion of expiration that is not deep lung air. The selective valve is connected to a mouthpiece that allows the user to breathe fresh air through the entire collection process via a one-way diaphragm valve. Exhaled anatomical dead space air enters the device through the mouthpiece and exits at the exhaust port. The exhaled deep lung air is then collected through the mouthpiece, enters the intake port, and is collected on the cooled collection plate of the device.

I.B. Collection Body Design for Efficient Condensation

With the aforementioned parameters in mind, a square perpendicular-facing flat plate coming from the T-Valve was designed. This body shape allows for a cooled aluminum plate with a large surface area (12.5 cm×13.3 cm; 166 cm2) to be attached the external face of the device to ensure the collection plate is maintained at sufficiently low temperatures (8 to 12° C.) for the entire duration of the test. The current body design is a large square frame with slots for an aluminum collection plate and a clear acrylic plate (both 13.4 cm×13.8 cm) with a 1.5 cm diameter hole that draws intake from the user directly from the collection port of the T-Valve. Once the breath has been condensed on the cooled collection plate, it can be wiped into a collecting centrifuge tube using a linear wiper that is manually pushed through the square container's collection area. The final design results in a streamlined device that is user friendly and efficient (FIG. 1).

II. Valve Actuation for Selective Collection

The initial period of exhalation characterized as dead space air must be removed to collect EBC that contains a large fraction of respiratory fluid. During a normal exhalation period, the transition from dead space air to deep lung air is characterized by a rise in $CO_2$ levels (as illustrated in normal capnography plots). Rather than using an expensive end-tidal $CO_2$ ($EtCO_2$) sensor, a system using an analog wind sensor and pneumatic valve actuator to measure temperature and wind-speed and selectively filter each exhalation in real-time was developed. Based on the valve actuation off of the temperature profile of exhaled breath; tests were conducted to confirm that the temperature and $CO_2$ profiles correlate well with each other. The Rev. C Wind Sensor (Modern Devices, Rhode Island, USA) was chosen because of its low-cost, compact design and excellent sensitivity and temporal resolution. It contains temperature and wind-speed pins that output a voltage based on the temperature and speed of passing air. An Arduino Uno microcontroller was set to sample pins at 200 millisecond intervals and convert voltages to corresponding digital values. The developed algorithm uses an experimentally-derived regression to produce accurate temperature and flow rate measurements and processes them to control valve actuation.

II.A. Temperature-Based Algorithm

Valve operation relies on a temperature-based algorithm which employs a dynamic calibration window to continuously update the temperature thresholds for valve actuation and adapt to changes in the breathing profile over the testing period. The algorithm uses either the minimum, average, or maximum temperature range of the last three breaths (based on user's discretion) to calculate a threshold increase in temperature. The valve opens when the difference between the current temperature and the temperature at the start of the exhalation period exceeds the calculated threshold and closes after two successive temperature decreases. The threshold temperature can be set to be within a percentage of the chosen temperature range observed within the last three breaths. Since the temperature profile matches the $CO_2$ profile, this allows for more accurate elimination of the dead-space period than a time-based algorithm alone.

II.B. Correlation of Temperature and $CO_2$ Profiles

To demonstrate the reliability of the temperature sensor over an end-tidal $CO_2$ meter, the temperature and $pCO_2$ profiles collected using the temperature sensor and the capnometer function of the RespirAct Gas Control System (Thornhill Medical, Toronto, Canada) were compared. The $pCO_2$, partial pressure of $CO_2$ gas in mmHg, directly relates to $CO_2$ concentration. For this test, the temperature sensor was embedded within the respiratory mask connected to the capnometer. Two healthy human subjects were asked to breathe deeply into the device and multiple trials of 3-minute breathing periods were recorded to collect $pCO_2$ and temperature profiles.

C. Actuation of Pneumatic Pressure Regulator

Figure 2:
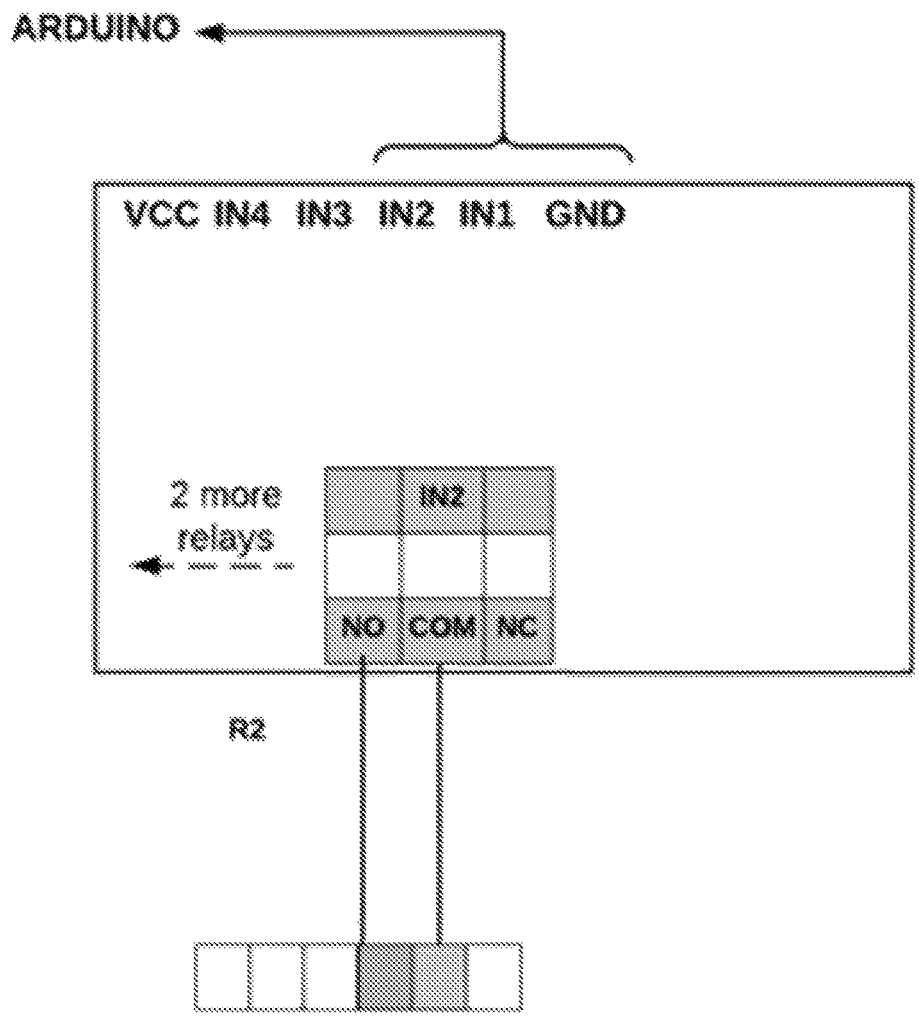
FIG. 2 is a circuit wiring of the four-relay module (shown are the two which are used in circuit), and valve actuation controller. The relays connected to pins inside the controller circuit board turn on/off pneumatic balloons to determine valve actuation.

The Arduino was interfaced with a Controller for Actuation of Inflatable Balloon-Type Automated Directional Control Valves (Hans-Rudolph, Kansas, USA) through a four-relay module as seen in FIG. 2. A compressed air supply is fed to the controller at approximately 40 psi. To actuate the valve, the balloon inflates to create a seal on the flow passage bore of the T-valve. The controller relies on one button to control the normally open (NO) pin that inflates balloon valve. The manual balloon valve controller was adapted by replacing the push-button pin connections with a circuit originating from one relay of the 4-relay module to control the switch (and subsequent valve actuation) based on the input from the Arduino. When the algorithm determines that the temperature has reached the appropriate threshold, it sets the relay to 'HIGH' to inflate the balloon and actuate the valve opening for collection into the intake port.

III. Threshold Optimization and Feasibility Studies

Two studies were conducted to 1) determine an appropriate selection threshold that can increase glucose content without compromising sample volume; and 2) optimize the collection procedure and establish a functional relationship between the feasibility, patient comfort, and sample volume found in the exhaled breath condensates.

III.A. Participants

Eight healthy subjects (ages 19-27) with no history of diabetes or lung-related diseases were examined. All subjects gave written consent to the experimental procedures, which had been approved by the Purdue University's Institutional Review Board.

B. Device Set-Up

Figure 3:
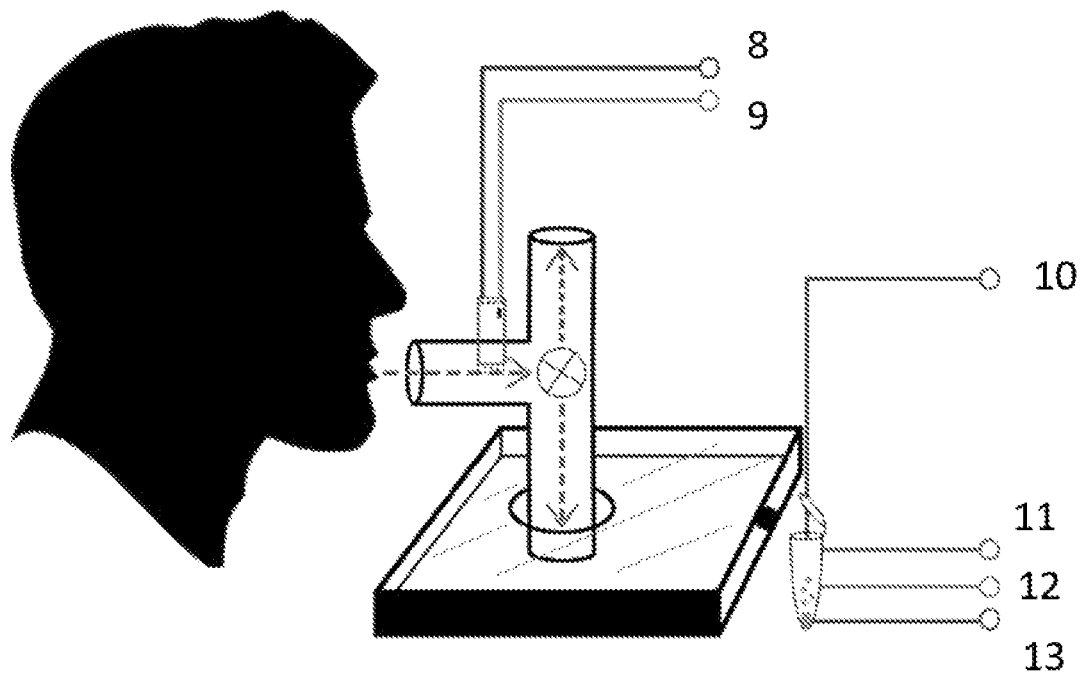
FIG. 3 is a device set-up for feasibility study data collection. For both studies, the temperature, valve actuation, time for collection, and total volume for each condensate sample was recorded. The first study also measured glucose content. The total protein concentration, pH, and glucose will be detected in clinical samples. (8. Valve actuation data; 9. Temperature data; 10. Glucose measurement; 11. Protein; 12. pH; 13. Volume)

Aluminum plates were cooled to 8° C. and were affixed to the back of the aluminum condensation plate to cool the surface prior to condensate collection. After 10 seconds of cooling, individuals breathed into a disposable mouthpiece designed to trap saliva that is connected to the intake port of the valve and the exhaled air was detected by the temperature/wind sensor (FIG. 3). The valve actuation begins after the initial calibration window and the code was programmed to stop collection after a specified volume of exhaled air was collected. The device set-up was similar for both studies.

C. Experiments

In the first study, five healthy subjects aged 23-27 years old (four female, one male) were examined. For 150 seconds of continuous breathing through the device, three exhaled breath condensate (EBC) samples were collected at three different threshold percentages: 0% (non-selective), 50%, and 80%. While total volume of exhaled air was not controlled, an average of 12 L was breathed into the device across all subjects. A commercial fluorometric glucose assay (Abnova, Taipei, Taiwan) was used to quantify glucose content. The concentrations and sample volumes were then compared using a t-test between two groups and ANOVA between all three groups to determine significant changes in glucose concentrations. In the same study, three additional samples were collected from same subjects to assess the consistency of sample volume collected. They were instructed to breathe normally through their mouths into the device until the program recorded that 15 L of exhaled air had been collected. The percentage threshold was set to 50% to minimize the collection of dead space air without compromising EBC sample volume. The time for collection, temperature data, valve actuation data, and total volume of condensate collected were recorded for each trial and analyzed for inter-subject and intra-subject variability using ANOVA.

In the second study, three healthy subjects aged 19-21 years old (two female, one male) were examined. EBC samples were collected for each subject in which they were instructed to breathe normally through their mouths into the device until the program recorded that either a) 7.5 L or b) 15 L of exhaled air had been collected. The percentage threshold used was either 0% (non-selective) or 70% to minimize the collection of dead space air without compromising EBC sample volume. For each combination of volume and threshold (4), three EBC samples were collected and analyzed for glucose content via the previously mentioned glucose assay. The total volume of condensate collected and glucose concentration were recorded for each trial and analyzed for inter-subject and intra-subject variability using ANOVA.

IV. Results and discussion

IV.A. Temperature and $CO_2$ Profile Comparison

Figure 4:
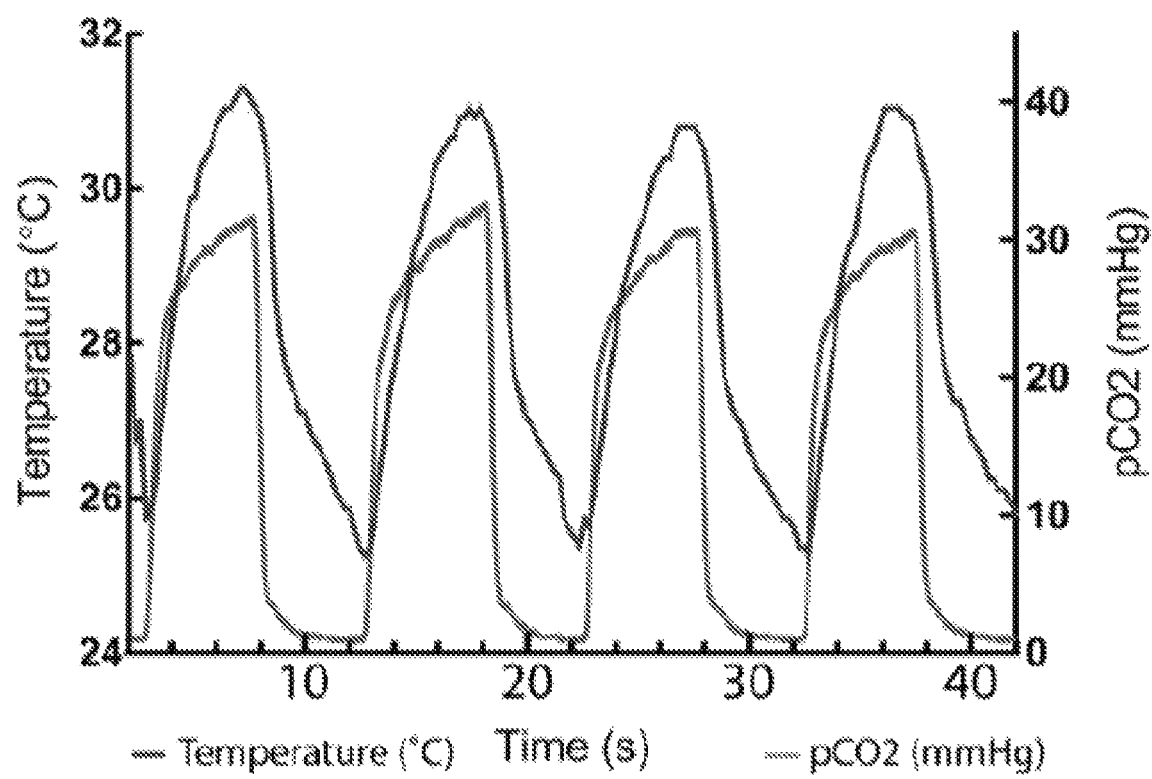
FIG. 4 is temperature and $CO_2$ profile comparison. Forty seconds of a three-minute breathing trial are displayed in the plot.

Human breathing profiles showed consistent, strong correlation between temperature and $CO_2$ data, as shown in FIG. 4. The $CO_2$ curve is characterized by a steep initial rise of $pCO_2$ followed by a plateau during exhalation and subsequent decrease during inhalation. The buildup of residual humidity and temperature may have affected the sensor's temporal resolution and thus prevented a plateau from forming on the temperature curve. However, the two profiles were generally well-correlated and there was little to no time lag observed. Therefore, we can conclude that a temperature sensor can be used for selective collection of deep lung air instead of a costly $EtCO_2$ meter.

IV.B Valve Actuation Algorithm for Selective Collection

Figure 5:
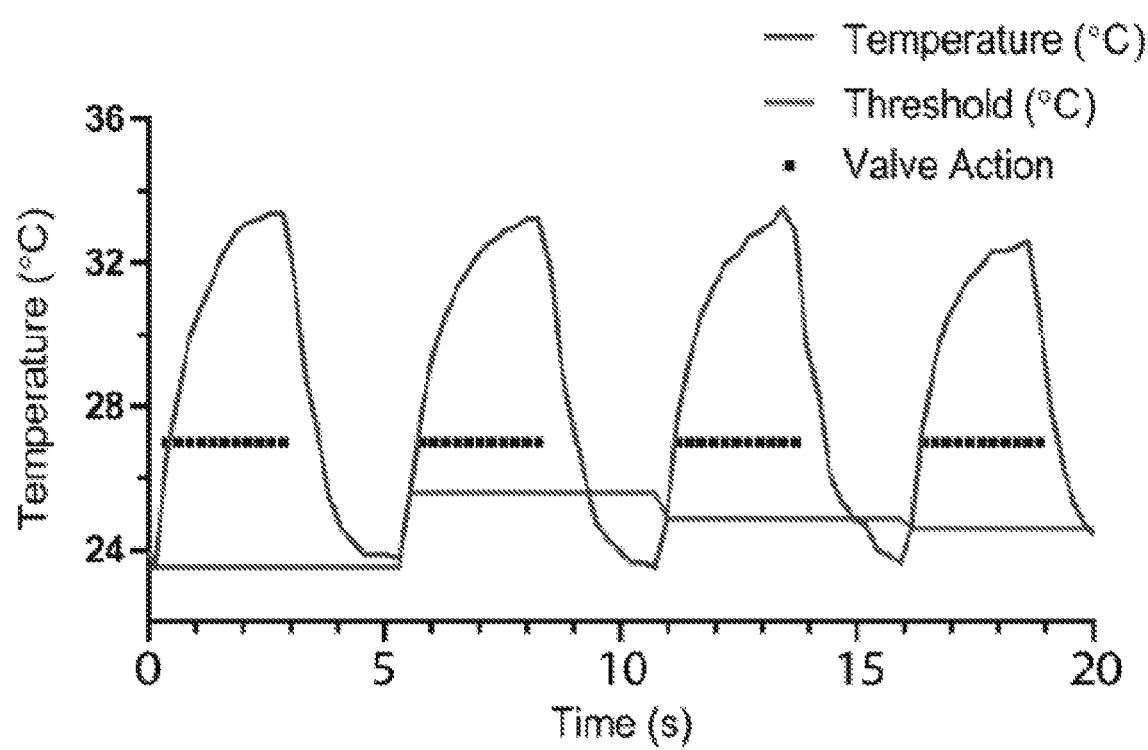
FIG. 5 is temperature-based valve actuation for one subject. The valve action (black) is displayed for periods where the valve is open.

The valve actuates simply based on the temperature threshold determined by the algorithm. FIG. 5 shows results from a trial taken from a healthy human subject in which the valve is programmed to open when the current temperature has crossed 40% of the calculated threshold range. The temperature threshold in green remains consistently within the temperature bounds of the breath.

IV.C. Threshold Optimization and Collection Feasibility

In the threshold optimization study, for a total of 15 L of exhaled breath collected, the device condensed 157±11 μL of EBC with non-selective actuation in 157±16 seconds; 139±17 μL with actuation at 50% in 174±9 seconds; and 84±4 μL with actuation at 80% in 190±19 seconds. No significant condensate loss was observed ($p > 0.05$, $n=3$) between the samples collected at 0% and 50% but collection at 80% significantly reduced the volume of sample collected ($p < 0.05$, $n=3$). When analyzed for glucose content, the samples collected at 50% and 80% produced significantly higher concentrations than the samples collected at 0% ($p < 0.05$). On average, the 80% threshold samples contained 13.6±0.1 μM compared to 3.6±0.2 μM and 9.0±0.3 μM from the 0% and 50% samples, respectively. While this is what we had hypothesized, a larger study with more participants and a randomized order of threshold collections would corroborate these results and correct for any confounding variables. The measurements should also be compared to a gold-standard detection system such as HPAEC-PAD to verify the accuracy of the concentrations. This study also demonstrated that the device can collect reproducible volumes of EBC with actuation at 50% ($p > 0.05$, $n=3$). On average, 135±47 μL of condensate was collected for 15 L of exhaled air; the average time for collection was 186±52 seconds. While there was no significant difference between the collection times ($p > 0.05$, $n=3$), it was observed that the time taken for collection did not correlate with the amount of condensate produced. This may be due to variability in subject's breathing patterns throughout the trials as deeper breaths may produce larger condensate volumes than shallow breaths; future experiments will further evaluate this effect.

In the second study, the glucose concentration of collected EBC samples was assessed against the presence of a selective threshold (0% vs. 70%) and against different total exhaled air volumes (either 7.5 L or 15 L). A threshold of 70% was chosen to produce better separation of alveolar and dead space air without compromising sample volume, as 80% threshold resulted in significant condensate volume loss. When the glucose concentration was assessed against just the threshold (regardless of total volume exhaled), there was an average 80% increase in glucose concentrations in samples collected with a 70% threshold. However, due to the large standard deviation across samples and the modest sample size, this difference was not significant ($p > 0.05$). When assessed against total exhaled air volumes (regardless of threshold), there was no significant difference in glucose concentrations across samples ($p > 0.05$). However, for samples condensed from 15 L of exhaled air, there is a marked increase in glucose concentration collected with the 70% threshold (0.65±0.36 μM) compared to samples collected non-selectively (0.24±0.16 μM). Based on these results, it can be assumed that a larger total exhaled volume can improve the device's ability to separate alveolar and dead space air. While this is not statistically significant, the preliminary results are promising and a larger sample size may demonstrate significance and smaller standard deviation. Thus, the selective collection of EBC based on temperature-based thresholds may concentrate solutes of interest in the collected sample. Future studies will assess glucose concentration vs. threshold for a larger and more diverse subject pool.

The temperature-based algorithm may be a computer program. An simplified version of a pseudocode is shown below:

Set-Up & Calibration Loops:

Read values for defined time period and volume total in specified increments (for example, read values every 200 milliseconds until either 250 seconds have passed or 12500 mL of exhaled breath has been collected If (minis( )>=0 && millis( )<250000 && volumeTotal<12500){

If (millis( )−lastMillis>200)

After first 200 ms, read input values from thermistor pin (TMP) and wind speed pin (RV) of sensor ReadInputs (analogPinforTMP, analogPinforRV)

Convert values into temperature (° C.) and volumetric flow rate (mL/s) based on experimentally derived regression calculations specific to the sensor Set previous temperature as 0° C.

Set offset to 0.1

Set calibration period to 15 seconds Set windPrev to 0 MPH

Main Loop:

If (current temperature>=previous temperature+offset)

{

Set max temperature to zero

Set counter to zero

Start counting iterations (+1) when an exhalation occurs (defined as increase in temperature profile when compared to inhalation)

If counter==1, set current temperature as initial temperature

For the rest of the exhalation (counter>1), if current temperature>max temperature, store current temperature as new max temperature If two successive temperature decreases are recorded, reset counter to zero and only increase count when a temperature increase occurs Update total volume exhaled by using the trapezoid rule to calculate total area under the curve of wind speed data currExhaled=(0.5×0.2 seconds*(WindSpeed_MPH+ windPrev))*(Tube cross-sectional area×0.595)* (1609.34×10000/36)

Set current WindSpeed_MPH to windPrev
*0.595 is the approximate fraction of the cross sectional area not covered by the sensor
}
If (time<calibration period)
{
Call the ThresholdUpdate( ) function
{
Store the temperature range (maximum temperature—initial temperature) for the last three exhalations in a 1×3 array and continuously update the last value and shift other two values to the left TeArray=[Range1,Range2,Range3]

The next updated array would look like this:

TeArray=[Range 2,Range 3,Range 4]

Etc. . . . until end of collection period (as defined in the setup and calibration loop)
Once a new temperature range is stored in the array, re-set the maximum temperature to zero and go back to previous loop to calculate maximum and initial temperatures for an exhalation period
For every three exhalations, set temperature threshold to be XX % of either the minimum, average, or maximum temperature range of the last three values in the array (user can choose what value to use)

tempThreshold=$XX$*(minTempRange)

or tempThreshold=$XX$*(averageTempRange)

or tempThreshold=$XX$*(maxTempRange)

}
If ((current temperature−initial temperature)>temperature threshold) AND (time>calibration period)
}
    Call the ThresholdUpdate( ) function
    Actuate the opening of the valve to allow breath to be collected in the intake port
        digitalWrite(valveaction, LOW)
        valveActTemp=1 (signifies valve opening)
        Keep the valve open until two successive decreases in temperature are recorded
            If two decreases are recorded, close the valve so that inhalation does not cause backflow of the collected breath
            digitalWrite(valveaction, HIGH)
            valveActTemp=0 (signifies valve closing)
}
Otherwise, keep the valve closed so that the exhaled breath that hasn't reached the threshold temperature (assuming this corresponds to dead space air) can escape through the exhaust port
Else}
    digitalWrite(valveaction, HIGH)
    Set valveActTemp=0 (signifies valve closing)
}

Those skilled in the art will recognize that numerous modifications can be made to the specific implementations described above. The implementations should not be limited to the particular limitations described. Other implementations may be possible.

We claim:

1. A device for selective collection of exhaled breath condensate, wherein the device comprises:
    a) mouthpiece configured to receive an exhaled breath from a human subject, wherein the exhaled breath comprises a first portion that is not deep lung air and a second portion that is deep lung air, wherein the deep lung air comprises at least one chemical to be detected;
    b) a first output configured to release the first portion of the exhaled breath that is not deep lung air;
    c) a second output configured to collect the second portion of the exhaled breath that is deep lung air, wherein the deep lung air comprises at least one chemical to be detected;
    d) a sensor for detecting a temperature;
    e) a valve, which is connected to the mouthpiece, the first output and the second output, wherein the valve is actuated by a temperature-based algorithm to selectively release the first portion of the exhaled breath, and selectively collect the second portion of the exhaled breath, wherein the valve opens into the second output when the difference between a current breath temperature and a breath temperature at the start of the exhalation period exceeds a calculated temperature threshold, and the valve closes after two successive decreases in the breath temperature, wherein the temperature threshold is calculated based on a temperature range of the last three breaths of the human subject; and
    f) a collection unit comprising a frame including (i) a plate, which is connected to the second output connected to the valve, (ii) a condensation plate, and (iii) a wiper, wherein the collection unit is configured to collect and condense the second portion of the exhaled breath and the wiper wipes the liquid from the collection unit.

2. The device of claim 1, wherein the chemical comprises glucose, nucleic acid, protein, peptide, lipid, inositol, cytokine, amylase, lipoarabinomannan, interferon gamma, nitrite, pathogen, hydrogen peroxide, opioid, nicotine salt, lactate, or any combination thereof.

3. The device of claim 1, wherein the chemical comprises glucose.

4. The device of claim 1, wherein the sensor can detect wind speed of a passing air flow.

5. The device of claim 1, wherein said condensation unit the collection unit has a temperature range of −20° C. to 15° C.

6. The device of claim 1, wherein the collection unit has a temperature range of 5° C. to 15° C.

7. The device of claim 1, wherein the device is portable and can collect and condense reproducible volumes of the exhaled breath under ten minutes.

8. The device of claim 1, wherein the valve is a pneumatic valve, a solenoid valve, or any valve that can be controlled to open and close to selectively control collection of the second portion of the exhaled breath.

9. A method of collecting at least one chemical to be detected, wherein the method comprises:
    providing a device of claim 1 to a human subject;
    collecting an exhaled breath from the human subject through a mouthpiece;
    actuating a valve by a temperature-based algorithm including:
        (i) selectively releasing a first portion of the exhaled breath which is not deep lung air, through a first output of the device; and
        (ii) selectively collecting a second portion of the exhaled breath, which is deep lung air, with a second output of the device, wherein the deep lung air comprises at least one chemical to be detected; and
    wherein the valve opens into the second output when the difference between a current breath temperature and a breath temperature at the start of the exhalation period exceeds a calculated temperature threshold, and the valve closes after two successive decreases in the breath temperature, wherein the temperature threshold is calculated based on a temperature range of the last three breaths of the human subject.

* * * * *